United States Patent
Jessop et al.

(10) Patent No.: US 7,097,449 B2
(45) Date of Patent: Aug. 29, 2006

(54) DENTAL BRACKETS FOR RETAINING A MEDICAMENT-RELEASING PELLET ON A TOOTH AND KITS INCLUDING SUCH BRACKETS

(75) Inventors: Neil Jessop, Sandy, UT (US); Bruce S. McLean, Sandy, UT (US); Paul Lewis, Midvale, UT (US); Dan Bills, Salt Lake City, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 56 days.

(21) Appl. No.: 10/793,145

(22) Filed: Mar. 4, 2004

(65) Prior Publication Data

US 2005/0196727 A1   Sep. 8, 2005

(51) Int. Cl.
*A61C 3/00* (2006.01)
(52) U.S. Cl. .............................. 433/8; 433/9; 433/229
(58) Field of Classification Search .................... 433/3, 433/4, 8, 9, 229; 424/464
See application file for complete search history.

(56) References Cited

U.S. PATENT DOCUMENTS

| | | | | |
|---|---|---|---|---|
| 4,039,653 A | * | 8/1977 | DeFoney et al. | 424/435 |
| 4,175,326 A | | 11/1979 | Goodson | 433/80 |
| 4,685,883 A | | 8/1987 | Jernberg | 433/215 |
| 4,764,377 A | | 8/1988 | Goodson | 424/435 |
| 4,861,268 A | | 8/1989 | Garay et al. | 433/229 |
| 5,049,077 A | * | 9/1991 | Goldin et al. | 433/229 |
| 5,074,786 A | * | 12/1991 | Woodward | 433/80 |
| 5,137,449 A | | 8/1992 | Goldin et al. | 433/229 |
| 5,437,872 A | | 8/1995 | Lee | 424/464 |
| 5,989,569 A | | 11/1999 | Dirksing et al. | 424/401 |
| 5,993,413 A | | 11/1999 | Aaltonen et al. | 604/77 |
| 6,036,943 A | | 3/2000 | Fischer | 424/49 |
| 6,086,855 A | | 7/2000 | Fischer | 424/49 |
| 6,106,286 A | | 8/2000 | Gupta | 433/80 |
| 6,126,443 A | | 10/2000 | Burgio | 433/215 |
| 6,264,469 B1 | * | 7/2001 | Moschik | 433/8 |
| 6,287,120 B1 | | 9/2001 | Wiesel | 433/215 |
| 6,326,022 B1 | | 12/2001 | Katz | 424/435 |
| 6,343,932 B1 | | 2/2002 | Wiesel | 433/215 |
| 6,435,873 B1 | | 8/2002 | Burgio | 433/80 |
| 6,482,002 B1 | * | 11/2002 | Jordan et al. | 433/9 |
| 6,506,053 B1 | | 1/2003 | Wiesel | 433/215 |
| 2002/0081555 A1 | | 6/2002 | Wiesel | |
| 2003/0003421 A1 | | 1/2003 | Bestenheider et al. | |

\* cited by examiner

*Primary Examiner*—Patricia Bianco
*Assistant Examiner*—Candice C. Stokes
(74) *Attorney, Agent, or Firm*—Workman Nydegger

(57) ABSTRACT

The present invention is directed to a dental bracket and associated kit used to attach a medicament-releasing pellet on a tooth. The kit is designed to provide slow release of fluoride or other medicament over a desired period of time. The medicament release kit includes a medicament-releasing pellet and a dental bracket. The bracket comprises a base and a socket configured to receive and retain the pellet at least partially therein. The device may be installed by a dental practitioner and remain attached to a patient's tooth for a few months or up to 20 years. The medicament-releasing pellet, designed to slowly release small quantities of fluoride or another medicament, may be replaced, for example, every 6 months to 2 years. Replacement of the medicament-releasing pellet may be performed at home or at a dentist's office.

22 Claims, 4 Drawing Sheets

DENTAL BRACKETS FOR RETAINING A MEDICAMENT-RELEASING PELLET ON A TOOTH AND KITS INCLUDING SUCH BRACKETS

BACKGROUND OF THE INVENTION

1. The Field of the Invention

The present invention is in the field of apparatus and methods for the slow release of a medicament, particularly, but not exclusively, fluoride for the improved treatment and/or prevention of dental caries. More particularly, the invention relates to brackets for retaining a medicament-releasing pellet on a tooth.

2. The Relevant Technology

Dental caries consist of demineralization of a tooth caused by bacteria. In the early stages of caries a white spot develops on the tooth and if the disease is not halted and reversed, the enamel surface breaks down to form a lesion. This can then lead to decay and eventually, a fractured or pitted tooth. It is well known that development of dental caries may be reduced by means of various factors, such as diet and oral hygiene measures, anti-microbial treatments and the application of fluoride to the teeth.

Current methods for administering fluoride include the fluoridation of drinking water, the ingestion of fluoride tablets or liquids, the incorporation of fluoride into mouth washes, dentifrices and foods, the topical application of fluoride solutions, gels and varnishes, and recently, the incorporation of fluoride in dental materials and special devices. These have a variable effect on caries which can be unpredictable on an individual basis and is dependent on patient compliance in following the prescribed regimen.

Evidence supports the efficacy of frequent applications of relatively low concentrations of fluoride ions for the elimination of caries. A sustained and controlled release delivery system could help to achieve this goal. At least three general approaches have been reported for the application of sustained and controlled slow releasing systems: (1) a sustained release ingested tablet or capsule (Masuhara et al. 1985); (2) incorporation of fluoride into dental cements (McClean & Wilson); and (3) an intra-oral device attached to the teeth (Minth et al. 1983). However, each of these existing technologies has been difficult to use, unpredictable, susceptible to damage, an irritant to surrounding tissue, or unacceptable to the patient.

BRIEF SUMMARY OF THE INVENTION

The present invention is directed to a bracket and medicament release kit that may be placed in the mouth of a patient. The bracket and kit are designed to provide slow release of fluoride or other medicament over a desired period of time.

According to one embodiment, the medicament release kit includes a medicament-releasing pellet and a bracket. The bracket comprises a base and a socket. The medicament-releasing pellet may have any of various shapes, such as spherical, ellipsoidal, loaf-shaped, bar-shaped, or any other shape that is able to fit within and be held by the bracket socket. It is preferable that the medicament-releasing pellet have a smooth surface and no sharp edges, although this is not required.

The pellet may be formed of amorphous or crystalline glass, light or chemically curable resins, thermoplastics, or other material that may be formed into a desirable shape. A medicament (e.g. fluoride) is incorporated into the pellet (e.g., as part of the forming material). One example of a glass material is a phosphorus based fluoride containing glass disclosed in U.S. application Ser. No. 10/069,143, which was filed Feb. 14, 2002, and which is incorporated herein by reference.

The bracket may be formed of a biocompatible material, for example plastic or a biocompatible metal, such as stainless steel or nickel-titanium. Plastics may be shaped using any known method including thermoplastic molding, thermosetting molding, and the like. When formed of metal, the device may be formed through stamping, cold forming, electro-chemical etching, or any combination thereof.

The base of the bracket is sized and configured to be attached to a patient's tooth. The base provides surface area in order to securely bond the bracket to a patient's tooth. According to one embodiment, the base may be flexible so as to better conform to the tooth surface. The base may be transparent or opaque. At least a portion of the base may be perforated. Perforations allow light to pass through to cure a light curable adhesive when the bracket is formed of an opaque material. Perforations also allow the adhesive to flow into the perforations, resulting in a better bond between the bracket and a patient's tooth.

According to one embodiment, the socket is sized and configured to receive a correspondingly-shaped medicament-releasing pellet. It may be formed so as to be flexible or rigid, as desired. Preferably, the medicament-releasing pellet fits tightly into the socket so as to minimize space between the pellet and the socket wall. Minimizing this space prevents food, bacteria, and other debris from lodging there and festering. The pellet may be inserted or removed by manipulating the socket with an instrument, such as a dental explorer.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the invention will now be provided with specific reference to figures illustrating preferred embodiments of the invention. It will be appreciated that like structures will be provided with like reference designations. To provide context for interpreting the scope of the invention, certain terms used throughout the application will now be defined.

As used herein, the terms "medicament-releasing pellet", "fluoride-releasing pellet", or "pellet" refer to compositions for slowly releasing a medicament (e.g., fluoride) into the body of a patient. The device may be formed of amorphous or crystalline glass, light or chemically curable resins, thermoplastics, or other materials that may be formed into a desirable shape. A medicament (e.g. fluoride) may be incorporated into the forming material. Such a device is capable of slowly releasing the medicament into a patient's body when placed in the patient's mouth.

The medicament release kit of the present invention is intended to be placed in the mouth of a patient. The kit is designed to provide slow release of fluoride or another medicament over a desired period of time. The "medicament release kit" includes a medicament-releasing pellet and a dental bracket configured to receive and retain the pellet. More particularly, the dental bracket comprises a base and a socket that is sized and configured to receive and hold a correspondingly sized and shaped pellet. According to one embodiment, the dental bracket may be placed in the mouth of a patient as a relatively permanent fixture (e.g., from a few months to up to 20 years), while the medicament-releasing pellet may be removed and replaced at regular intervals, for example once each year.

Figures 1A, 1B:
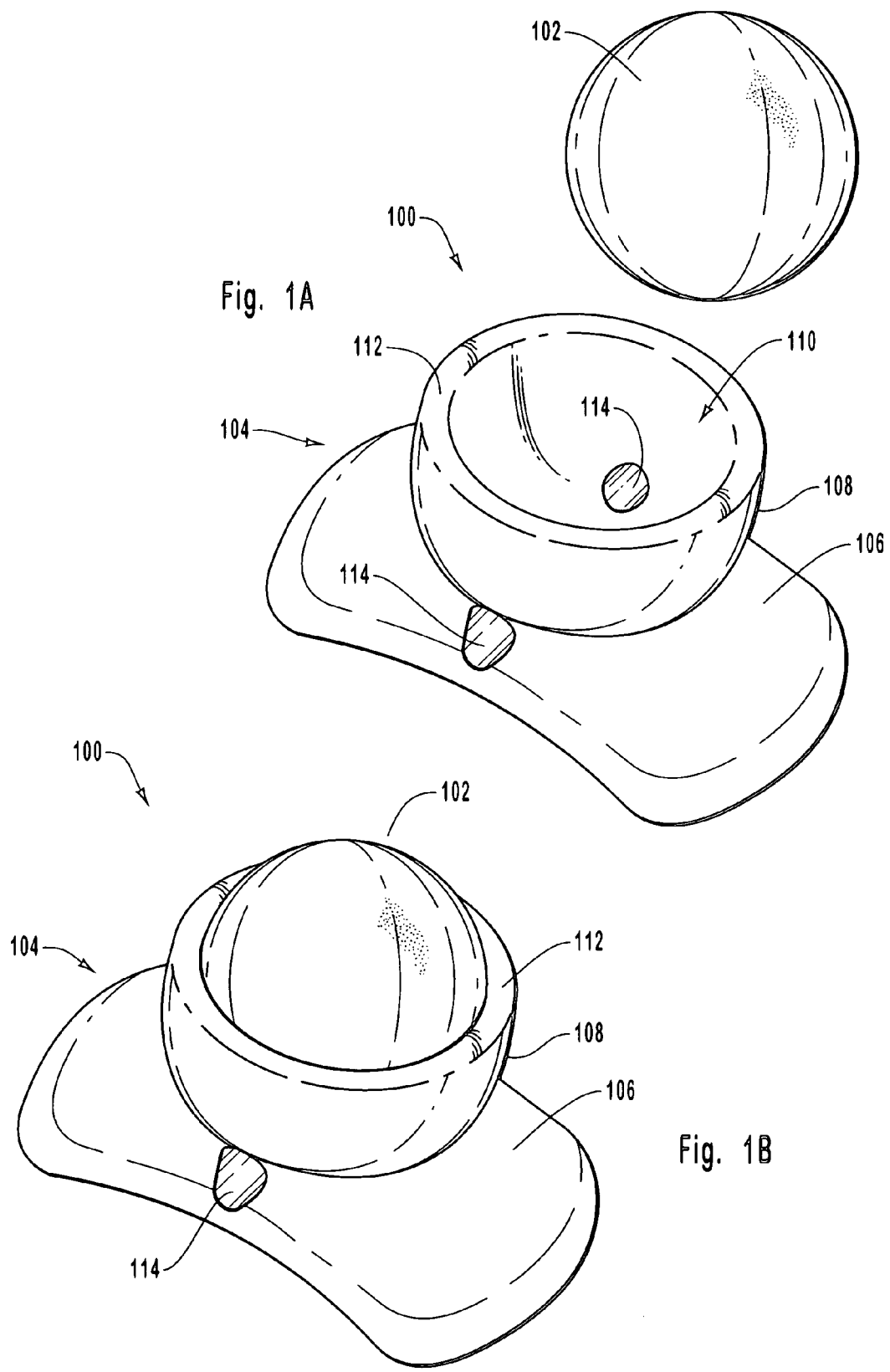
FIG. 1A is a perspective view of an exemplary dental bracket shown with a medicament-releasing pellet, which together comprise a medicament release kit.
FIG. 1B is a perspective view of the exemplary medicament release kit of FIG. 1A but with the medicament-releasing pellet inserted and held within a socket of the dental bracket.

Attention is now directed to the drawings. FIGS. 1A and 1B illustrate an exemplary medicament release kit 100. The kit includes a medicament-releasing pellet 102 and a dental bracket 104. The bracket 104 includes a base 106 and a socket 108. The base 106 is configured so as to be attached (e.g., by bonding) to a person's tooth (e.g., molar) The socket 108 is configured to receive and retain at least partially therein medicament-releasing pellet 102. FIG. 1A is a perspective view illustrating the medicament release kit 100 with the pellet 102 separate from the bracket 104, while FIG. 1B illustrates the same medicament release kit 100 with the pellet 102 received and held within the socket 108 of dental bracket 104.

The medicament-releasing pellet 102 shown in FIGS. 1A and 1B has a spherical shape, although any of various other shapes, such as ellipsoidal, loaf-shaped, bar-shaped, or any other shape may be used. The medicament-releasing pellet 102 contains a medicament (e.g. fluoride) that is slowly released into the patient's body over a period of time. For example, where the medicament is fluoride, it may be slowly released over a period between 6 months and 2 years.

The pellet may be formed of amorphous or crystalline glass, light or chemically curable resins, thermoplastics, or other materials. An example of a suitable glass composition is a phosphorus-based, fluoride-containing glass disclosed in U.S. application Ser. No. 10/069,143, filed Feb. 14, 2002, and which was previously incorporated by reference. Such glass compositions can be formed into a pellet (e.g., by being fused) and once placed in the patient's mouth, will slowly release the fluoride or other medicament contained in the pellet over time. Thermoplastics or curable resins may be desirable pellet forming materials where the medicament decomposes or is otherwise destroyed at high temperatures such as those that may be required to form a glass. In the case of fluoride, the pellet 102 may be replaced once the concentration of fluoride in the patient's mouth begins to decrease below a desired standard. For example, the pellet may be removed and replaced after a period of as little as 6 months or as long as 2 years.

The dental bracket 104 includes a base 106 and a socket 108. Although illustrated without perforations formed in the base 106, perforations may be present or not present, as desired. The base 106 is configured so as to be bonded to the surface of a patient's tooth. The base 106 advantageously provides sufficient surface area for bonding, which results in a strong bond to the patient's tooth. Perforations (not shown) may be included to facilitate bonding of the device 104 as they may be configured to allow adhesive to flow through the perforations, providing a better bond between the device 104 and the patient's tooth.

In one embodiment, the device 104 may be designed so as to be attached to a patient's tooth for a relatively long period of time. Preferably, the bracket is bonded so as to remain attached to the patient's tooth for up to 5 years, more preferably up to 10 years, and most preferably up to 20 years. According to one embodiment, the base 106 may be bonded to a tooth with a chemical cure or light cure adhesive resin.

The socket 108 may have any desired size, shape or configuration in order to receive and at least partially retain therein a medicament-releasing pellet (e.g., pellet 102). In one embodiment, the socket 108 includes a hollow interior 110 defined by inner surfaces of the socket 108. The hollow interior 110 is advantageously sized and configured to receive at least a portion of a pellet (e.g., pellet 102) in a manner so that the pellet is securely retained by the socket 108. In one embodiment, the socket 108 includes an outer rim 112 having a diameter that is smaller than the diameter of the interior portion 110. This allows the portion of the pellet 102 having the largest diameter to be positioned within the interior portion 110 of the socket in a manner so that the outer rim 112 overhangs the largest diameter portion of the pellet 102. In this way, the outer rim 112 of the socket mechanically retains the pellet 102 at least partially within the interior portion 110 of the socket 108.

In the illustrated embodiment, the socket 108 may further include one or more auxiliary holes 114, which can be positioned so as to enable a dental practitioner to pry the medicament-releasing pellet 102 from the socket 108 using a dental explorer or other instrument. The socket 108 may be formed of a rigid or flexible material. A flexible material allows for easier insertion and withdrawal of the pellet 102 from the socket 108. Preferably, the medicament-releasing pellet 102 fits tightly within the interior portion 110 of the socket 108 so as to minimize space between the pellet 102 and the inner wall of socket 108. Minimizing space prevents food, bacteria, or other debris from lodging and festering therein. The dental bracket 100 may be designed so as to permit removal and replacement of the pellet 102 at home or at a dentist's office.

According to one embodiment, the base and socket of brackets according to the invention may be formed of a thin, resilient, biocompatible material, for example plastic, stainless steel, or nickel-titanium. A preferred material is a urethane plastic because of its exceptional compatibility with light curable adhesives. When formed of metal, the device may be formed through a combination of stamping and cold forming, while perforations (if present) may be formed by electrochemical etching. In a preferred embodiment, the base and socket are manufactured as a single piece, although they may be formed as two initially separate pieces and then joined together as desired.

Figure 2:
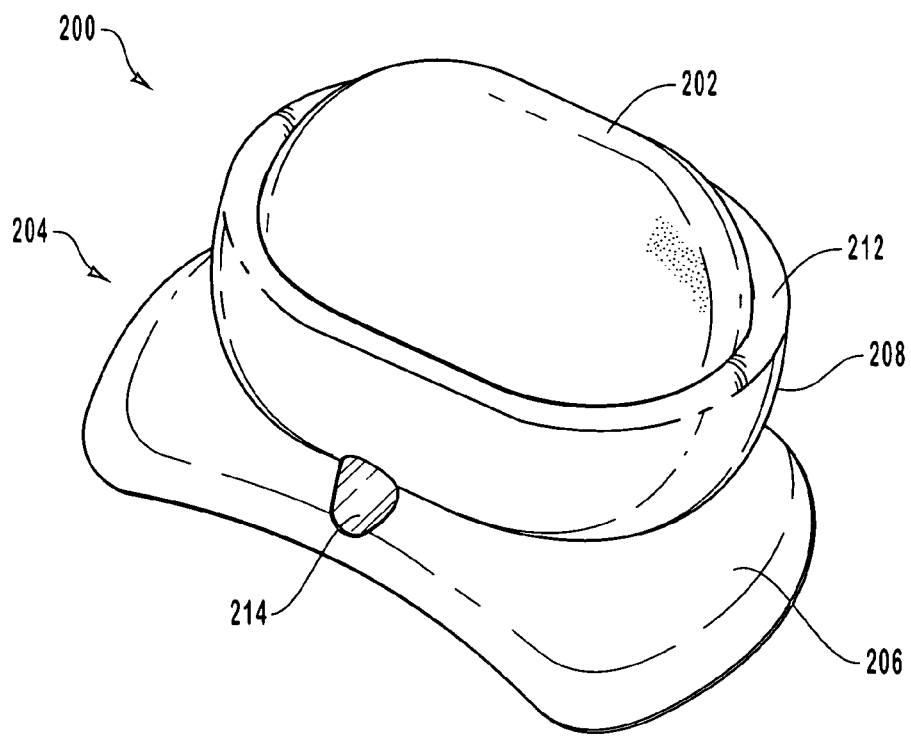
FIGS. 2–4 are perspective views of various alternative exemplary medicament release kits having differently-shaped medicament releasing pellets and correspondingly sized sockets.

FIG. 2 illustrates an alternative medicament release kit 200 having an ellipsoidal medicament-releasing pellet 202 and a dental bracket 204. Bracket 204 includes a base 206 and a socket 208 that includes an ellipsoidally-shaped outer rim 212 and an interior portion (not visible) that is configured to receive at least partially therein the ellipsoidal pellet 202. FIG. 2 illustrates the pellet 202 received within socket 204 and mechanically retained by the outer rim 212. The socket 208 may also include one or more auxiliary holes 214 to enable a dental practitioner to pry the medicament-releasing pellet 202 from the socket 208 using a dental explorer or other instrument.

Figure 3:
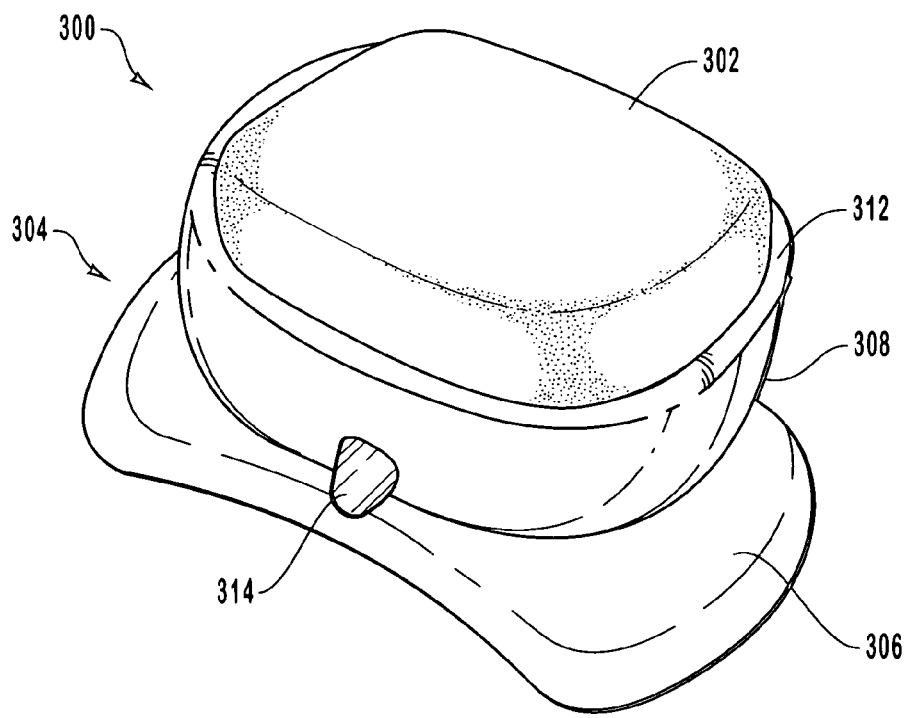

FIG. 3 illustrates an alternative medicament release kit 300 comprising a bar-shaped medicament-releasing pellet 302 and a dental bracket 304. Bracket 304 includes a base 306 and a socket 308 that includes an outer rim 312 and an interior portion (not visible) that is configured to receive at least partially therein the bar-shaped pellet 302. The socket 308 may also include one or more auxiliary holes 314 to enable a dental practitioner to pry the medicament-releasing pellet 302 from the socket 308 using a dental explorer or other instrument.

Figure 4:
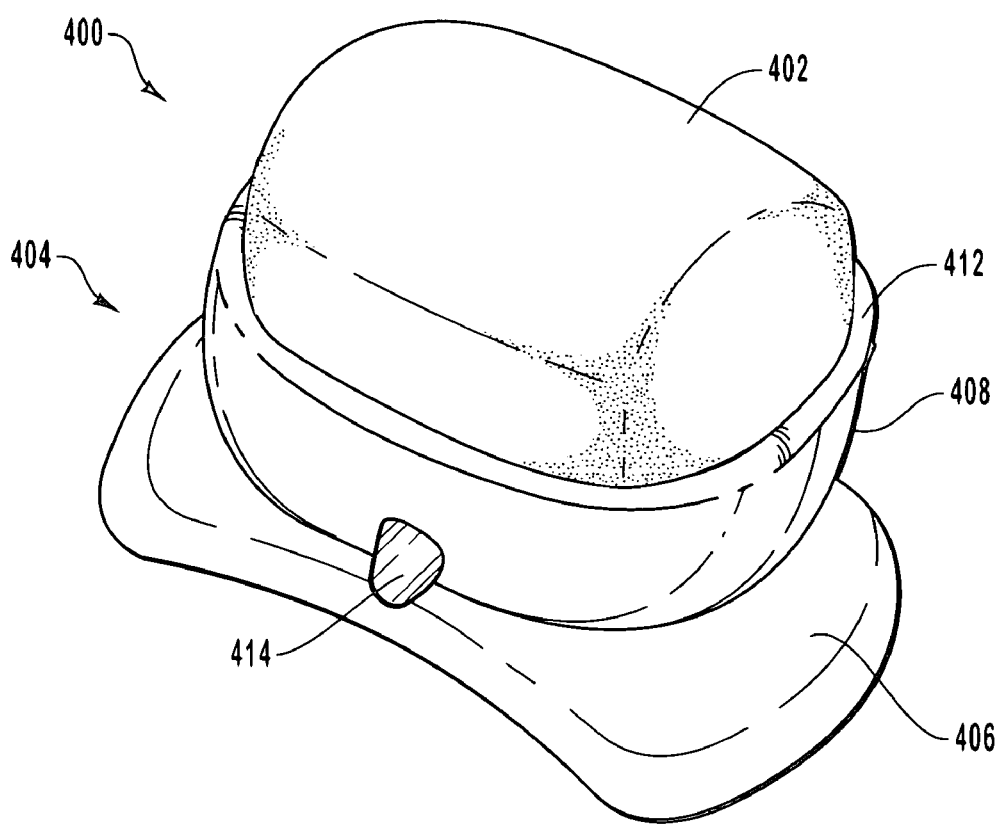

FIG. 4 illustrates another alternative medicament release kit 400 comprising a loaf-shaped medicament-releasing pellet 402 and a dental bracket 404. Bracket 404 includes a base 406 and a socket 408 that includes an outer rim 412 and an interior portion (not visible) configured to receive at least partially therein the loaf-shaped pellet 402. FIG. 4 is a perspective view of the kit 400 with the pellet 402 received within socket 408. The socket 408 may also include one or more auxiliary holes 414 to enable a dental practitioner to pry the medicament-releasing pellet 402 from the socket 408 using a dental explorer or other instrument.

Figure 5:
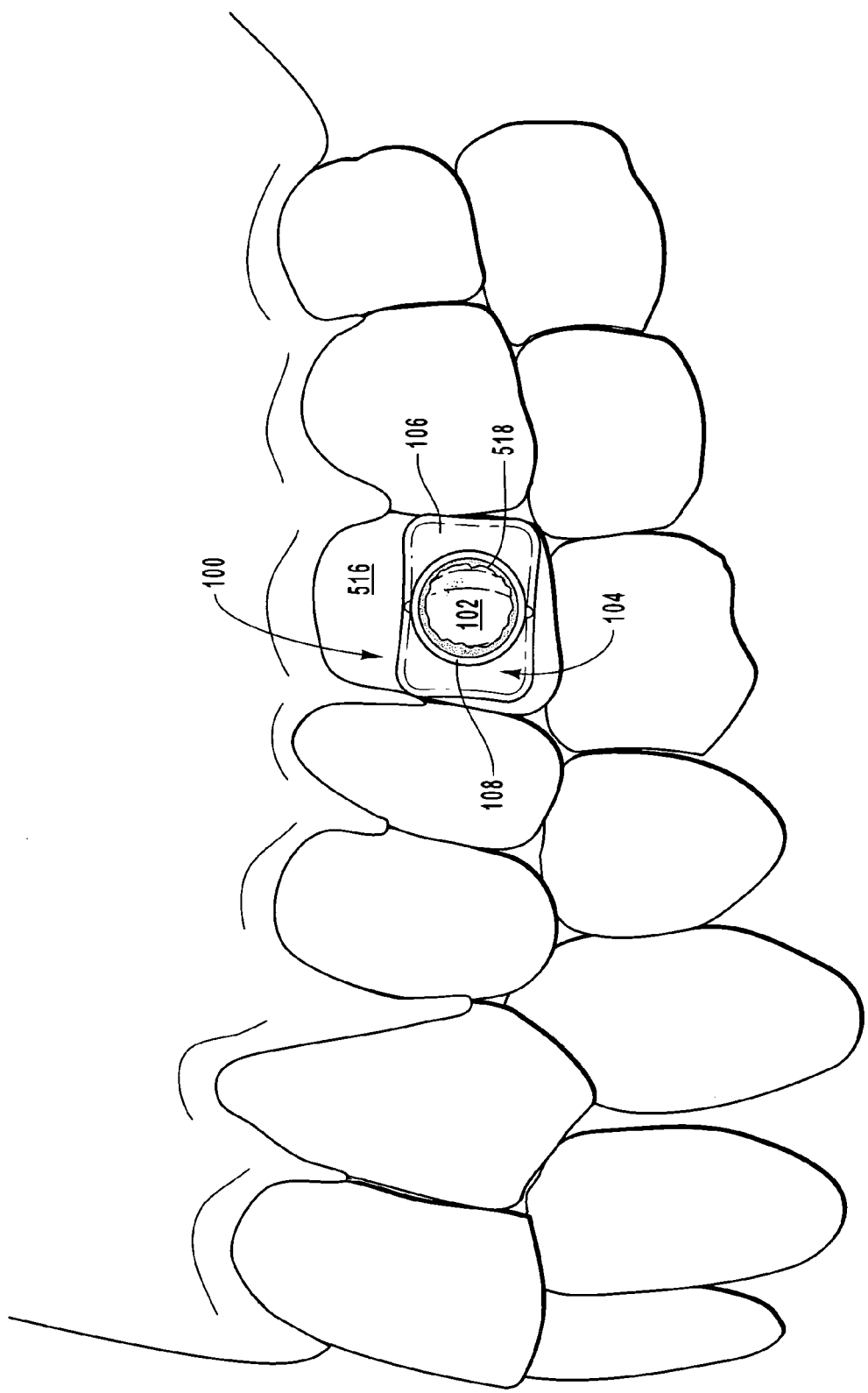
FIG. 5 illustrates the dental bracket of FIG. 1A bonded to a patient's tooth holding a medicament-releasing pellet within the socket of the dental bracket.

The dental bracket may be attached to a patient?s tooth, as illustrated in FIG. 5, using any desired attachment means. FIG. 5 more particularly illustrates the attachment of the dental bracket 104 of kit 100 as illustrated in FIGS. 1A-1B, although any of the other exemplary embodiments may be similarly attached. This may be done using any suitable adhesive (e.g., a chemical or light curable adhesive resin). In one embodiment, the bonding side of the base 106 of dental bracket 104 may have-the first part of a two-part chemical cure adhesive resin pre-applied. In another embodiment, the bonding side may have a light-activated resin pre-applied. Pre-applying the adhesive resin aids the dental practitioner in ease of use and placement.

The adhesive may be chemical cured, light cured, or air cured as desired in order to securely bond the dental bracket 104 to the tooth 516. With the adhesive in place (whether pre-applied or applied by the dental practitioner), the dental bracket 104 (with or without a pellet 102 within socket 108) is placed on a tooth 516. The base 106 provides sufficient surface area for bonding the bracket 104 to the tooth 516. According to one embodiment, the base 106 is sufficiently curved and flexible so as to more closely correspond to the contour of the tooth 516.

The medicament-releasing pellet 102 may be held within the socket 108 by a friction fit, by manipulating the socket 108 so as to grip and contact pellet 102 (e.g., the rim 112 retains the pellet 102 at least partially within interior portion 110 (see FIGS. 1A and 1B)), or by placing a bead of adhesive 518 (e.g., silicone resin) between the socket 108 and the pellet 102 as illustrated in FIG. 5.

As illustrated in FIG. 5, the device may be bonded to the patient's first upper molar according to one embodiment, although other positions or teeth could be used. In addition, it may be desirable in some cases to install more than one bracket or kit within the patient's mouth. For example, separate brackets or kits may be attached to each of the upper and lower first molars.

The dental bracket of the kit may be installed by a dental practitioner so as to remain installed in the patient's mouth over a long period of time (e.g., from a few months up to 20 years). The medicament-releasing pellet is intended to provide slow release of a medicament (e.g. fluoride) over a period between about 6 months and about 2 years, after which time the pellet may be removed and replaced, either at home or at a dentist's office.

Other medicaments may be included within medicament-releasing pellets according to invention in addition to, or instead of, fluoride. Non-limiting examples include antimicrobial agents, anti-tartar agents, anti-plaque agents, anesthetics, desensitizing agents, tooth whitening agents, vitamins, minerals, other nutrients, and/or mouth freshening agents known in the art.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A dental bracket designed to receive therein a fluoride or other medicament-releasing pellet, comprising:
   a base configured for attachment to a tooth surface; and
   a socket including an outer rim and an interior portion, the outer rim having a diameter or width that is less than a maximum diameter or width of the interior portion such that the outer rim overhangs part of the interior portion, the outer rim, because it overhangs part of the interior portion of the socket, also partially overlapping and thereby securely mechanically retaining a pellet when inserted within the interior portion of the socket.

2. A dental bracket as recited in claim 1, wherein at least a portion of the base is perforated.

3. A dental bracket as recited in claim 1, wherein the base and socket are formed as a single piece.

4. A dental bracket as recited in claim 1, further comprising at least one auxiliary hole for aiding a dental practitioner in removing a medicament-releasing pellet from the socket.

5. A dental bracket as recited in claim 1, wherein the base is flexible so as to be conformable to the contour of a patient's tooth.

6. A dental bracket as recited in claim 1, wherein the bracket is formed of a plastic material.

7. A dental bracket as recited in claim 6, wherein the plastic material comprises a urethane.

8. A dental bracket as recited in claim 1, wherein the base is formed of a metal comprising at least one of stainless steel and nickel-titanium.

9. A dental bracket as recited in claim 8, wherein the base is formed by stamping, cold forming, electrochemical etching, or combinations thereof.

10. A dental bracket as recited in claim 1, further comprising an adhesive applied to the base.

11. A dental bracket as recited in claim 1, wherein the socket is substantially circular or partially spherical.

12. A dental bracket as recited in claim 1, wherein the socket is substantially elliptical or ellipsoidal.

13. A medicament release kit comprising:
a dental bracket as recited in claim 1; and
a medicament-releasing pellet that is sized and configured so as to be securely retained within the socket of the dental bracket.

14. A medicament release kit as recited in claim 13, wherein the medicament-releasing pellet is formulated so as to release fluoride when continuously exposed to saliva.

15. A medicament release kit as recited in claim 13, wherein the medicament-releasing pellet is formulated so as to release at least one medicament selected from the group comprising antimicrobial agents, anti-tartar agents, anti-plaque agents, anesthetics, desensitizing agents, tooth whitening agents, vitamins, minerals, nutrients, and mouth freshening agents.

16. A medicament release kit as recited in claim 13, wherein the medicament-releasing pellet is substantially spherical or circular.

17. A medicament release kit as recited in claim 13, wherein the medicament-releasing pellet is elliptical, ellipsoidal, bar-shaped or loaf-shaped.

18. A method of installing a medicament-releasing pellet within a patient's mouth, comprising:
(a) providing a medicament release kit comprising:
　　a dental bracket designed to receive therein a medicament-releasing pellet comprising:
　　　a base configured for attachment to a tooth surface, the base including a bonding surface; and
　　　a socket that is sized and configured to receive therein a correspondingly-sized and shaped pellet; and
　　a medicament-releasing pellet
(b) bonding the bonding surface of the base of the dental bracket to the patient's tooth using a curable adhesive resin that is cured by at least one of chemical curing, light curing or air curing;
(c) applying an adhesive to at least one of the socket or medicament-releasing pellet; and
(d) inserting the medicament-releasing pellet at least partially within the socket of the dental bracket in order for the adhesive resin to bond the medicament-releasing pellet within the socket.

19. A method as recited in claim 18, wherein (d) is performed prior to (b).

20. A method as recited in claim 18, wherein (b) is performed prior to (d).

21. A method as recited in claim 18, wherein the adhesive used to bond the medicament-releasing pellet within the socket comprises a silicone resin.

22. A dental bracket as recited in claim 1, the socket being positioned on the base so as to extend labially relative to a tooth to which the base is attached during use in order to permit insertion of a pellet into the socket after attachment of the base to a tooth.

* * * * *

UNITED STATES PATENT AND TRADEMARK OFFICE
CERTIFICATE OF CORRECTION

PATENT NO. : 7,097,449 B2  
APPLICATION NO. : 10/793145  
DATED : August 29, 2006  
INVENTOR(S) : Jessop et al.

Page 1 of 1

It is certified that error appears in the above-identified patent and that said Letters Patent is hereby corrected as shown below:

Column 3  
Line 40, after "molar)" insert --.--

Column 4  
Line 55, change "100" to --104--

Column 5  
Line 10, change "204" to --208--  
Line 36, change "patient?s" to --patient's--  
Line 44, change "have-the" to --have the--

Signed and Sealed this

Thirtieth Day of January, 2007

JON W. DUDAS  
*Director of the United States Patent and Trademark Office*